(12) United States Patent
Briegel et al.

(10) Patent No.: US 8,044,237 B2
(45) Date of Patent: *Oct. 25, 2011

(54) METHOD FOR PRODUCTION OF AQUEOUS (METH)ACRYLIC ACID

(75) Inventors: Keith F. Briegel, Houston, TX (US);
Michael Stanley DeCourcy, Houston, TX (US); James Elder, Houston, TX (US); James Jerrick Juliette, Houston, TX (US); Joy Lydon Mendoza, Lansdale, PA (US)

(73) Assignee: Rohm and Haas Company, Philadelphia, PA (US)

( * ) Notice: Subject to any disclaimer, the term of this patent is extended or adjusted under 35 U.S.C. 154(b) by 271 days.

This patent is subject to a terminal disclaimer.

(21) Appl. No.: 12/455,361

(22) Filed: Jun. 1, 2009

(65) Prior Publication Data
US 2009/0299095 A1    Dec. 3, 2009

Related U.S. Application Data

(60) Provisional application No. 61/130,349, filed on May 30, 2008.

(51) Int. Cl.
*C07C 51/42* (2006.01)
(52) U.S. Cl. ........................................................ 562/600
(58) Field of Classification Search ........................ None
See application file for complete search history.

(56) References Cited

U.S. PATENT DOCUMENTS

2001/0016668 A1*   8/2001   Mitsumoto et al. ........... 562/600
* cited by examiner

*Primary Examiner* — Karl J Puttlitz
(74) *Attorney, Agent, or Firm* — Marcella M. Bodner

(57) ABSTRACT

The present invention relates to recovery of aqueous (meth)acrylic acid by condensation of a (meth)acrylic acid-containing stream to produce aqueous (meth)acrylic acid having a higher concentration of (meth)acrylic acid and a lower concentration of formaldehyde, i.e., not more than 0.1 weight %, than the aqueous (meth)acrylic acid produced using hitherto-fore known separation methods. The (meth)acrylic acid-containing stream may be the raw product stream of catalytic oxidation at least one $C_2$-$C_4$ alkane or alkene.

8 Claims, 1 Drawing Sheet

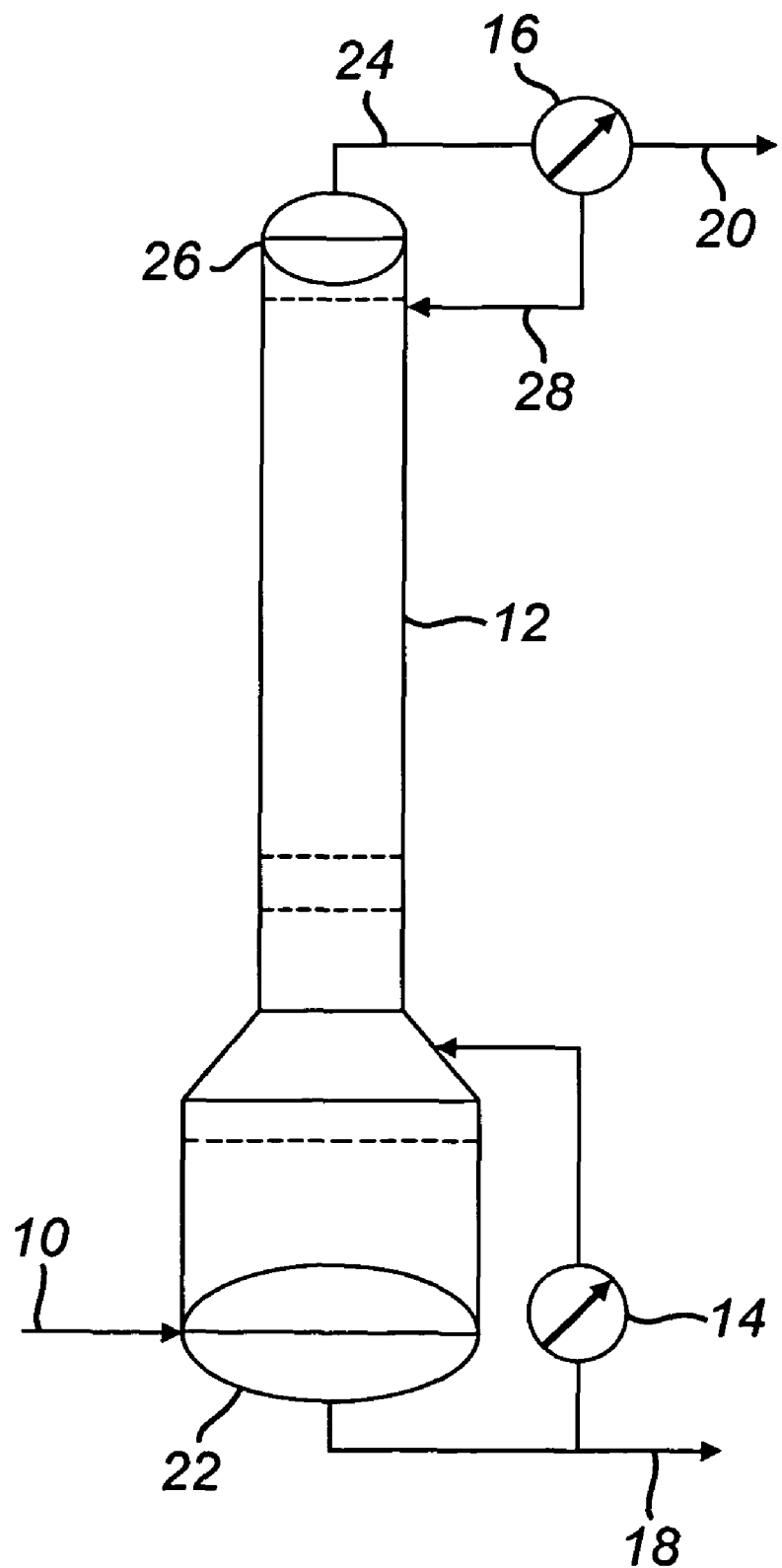

METHOD FOR PRODUCTION OF AQUEOUS (METH)ACRYLIC ACID

This invention claims priority to U.S. Provisional Application No. 61/130,348 filed May 30, 2008.

FIELD OF THE INVENTION

The present invention relates to recovery of (meth)acrylic acid from a gaseous material stream to produce aqueous (meth)acrylic acid.

BACKGROUND OF THE INVENTION

Monomers, such as unsaturated carboxylic acids and unsaturated nitrites, are industrially important as starting and intermediate materials for producing various synthetic resins, coating materials, fibers, plasticizers, synthetic resins, and the like. Commercially, there are various processes for producing unsaturated carboxylic acids (e.g., acrylic acid and methacrylic acid) and unsaturated nitriles (e.g., acrylonitrile and methacrylonitrile), but broadly, all such processes begin in essentially the same manner, via the catalytic reaction of one or more hydrocarbons to produce an impure gaseous material comprising the desired monomer. It is then necessary to recover the desired monomer from the impure gaseous material, and then to further purify it in order to minimize the amount of other materials, by-products, and impurities present in the recovered monomer stream.

For example, one well-known and commercially successful process for acrylic acid manufacture involves a two-step vapor phase catalytic oxidation reaction wherein propylene is converted first to acrolein in a first process step, and the acrolein is then converted to acrylic acid in a second process step. The resulting gaseous material stream comprises acrylic acid, but also water, unreacted propylene and acrolein, and several by-products including, but not limited to, one or more of the following compounds: formaldehyde, acetic acid, propionic acid, benzaldehyde, furfural, and maleic acid. Another known process which is currently being explored and developed is the single step vapor phase catalytic oxidation of propane in the presence of a suitable catalyst, and which also produces a gaseous material stream comprising acrylic acid, water, carbon oxides, unreacted propane, propylene, acrolein and several by-products including, but not limited to, one or more of the following compounds: formaldehyde, acetic acid, propionic acid, benzaldehyde, furfural, and maleic acid.

Regardless of the reaction process which produces it, aqueous acrylic acid is then most typically recovered from the raw gaseous product stream in an absorption tower, wherein a cooled absorbent, such as water or an organic compound (e.g., diphenyl ether) directly contacts the gaseous material stream, simultaneously condensing and absorbing various components, including acrylic acid and water, from the gaseous material stream to produce an aqueous acrylic acid stream. This aqueous mixture typically contains appreciable amounts of by-products and impurities such as acrolein, formaldehyde, and water. This is, at least in part, because direct-contact absorption processes also capture by-products and impurities with the (meth)acrylic acid from the gaseous (meth)acrylic acid-containing material, rather than only the desired (meth)acrylic acid product. For this reason, it is common for the resulting aqueous acrylic acid stream to be subjected to one or more purification steps. The intended use for the acrylic acid will often determine the degree to which the material stream must be purified and the extent to which the other materials must be removed or separated from the acrylic acid.

Purification, or separation, of the desired acrylic acid product from other materials in the aqueous acrylic acid stream may be accomplished by one or more well-known and understood processes including distillation, extraction, and/or crystallization. One of the most common of these purification steps is the use of azeotropic distillation to remove water from the aqueous acrylic acid stream. The purification of aqueous acrylic acid streams via azeotropic distillation is well known in the art of acrylic acid production. Various azeotropic distillation processes have been developed over the years based upon different azeotropic agents, for example U.S. Pat. No. 3,798,264 teaches the use of isobutyl acetate (IBAc) as the azeotropic agent, GB Patent No. 2146636 teaches the use of methyl isobutyl ketone (MIBK) as the azeotropic agent, and U.S. Pat. No. 6,399,817 teaches the use of toluene as the azeotropic agent.

Further purification processes, such as multiple distillation steps in series, or crystallization processes, are often necessary to meet final product quality requirements. Of course, each additional purification step requires additional initial capital investment, as well as higher operational costs.

For example, the process disclosed in U.S. Pat. No. 6,482,981 involves absorption of (meth)acrylic acid by direct contact of the material stream with water, followed by azeotropic distillation, and then by crystallization of the resulting aqueous acrylic acid to remove additional impurities and thereby minimize polymerization and formation of other solids. Such a complex process is therefore economically unattractive to construct and operate.

It is important to note that some of the by-products and impurities in the aqueous acrylic acid stream may interfere with the operation and efficiency of downstream processes, such as further purification, storage, or reaction to produce other materials (e.g., esters of (meth)acrylic acids). For example, as explained in U.S. Patent Application Publication No. US 2007/0167650, high levels of formaldehyde in acrylic acid streams interact adversely with some polymerization inhibitors (e.g., phenothiazine ("PTZ"), hydroquinone ("HQ"), and monomethyl ether of hydroquinone (MeHQ")) resulting in formation of solid precipitates in the acrylic acid product. This reaction also reduces the effectiveness of the inhibitor molecules in preventing polymerization of the acrylic acid monomer, since some of the inhibitor is consumed in forming the solid precipitates. Further, these effects worsen with increasing temperatures, such as are often used in azeotropic distillation columns. It would therefore be advantageous to remove as much of these impurities as possible at the recovery step, prior to downstream purification of the aqueous acrylic acid. Unfortunately, the disclosure of U.S. Patent Application Publication No. US 2007/0167650 does not provide guidance for removing such impurities. Instead, the application only proposes that one limit, i.e., reduce, the concentration of inhibitors in the process to avoid the formation of precipitates. Such an approach is clearly at odds with reliable process operation, as it obtains reduced precipitate formation at the cost of insufficient process inhibition.

As an alternative to conventional absorption with water or organic absorbents, U.S. Pat. No. 6,646,161 describes a process for recovering (meth)acrylic acid from a hot gas containing (meth)acrylic acid and a high proportion of non-condensable constituents, by "fractional condensation" of the hot gas. The desired aqueous acrylic acid product (having greater than 95% by weight acrylic acid) exits from the side of the fractional condenser, while light ends (uncondensed components) exit from the top and the heavier impurities and by-products exit as a condensed liquid stream from the bottom. Thus, the process of U.S. Pat. No. 6,646,161 produces an aqueous acrylic acid product, and at least two by-product streams which must be handled separately. Optionally, a wastewater stream may be withdrawn from the side of the fractional condenser, further increasing the acrylic acid content of the aqueous acrylic acid side stream, but also creating a third by-product stream which must be processed. The fractional condenser used in this process is divided into "sections" to solve various engineering problems (i.e., separation of multiple components whose boiling points differ by greater than 25° C.) and accomplishes simultaneous cooling of the hot gas and condensation of the higher boiling fraction thereof. Thus, this process may be considered a combination of rectification and absorption which is often accomplished in two separate steps in conventional processes. The benefits of obtaining a purified acrylic acid stream from such a process are outweighed, however, by the substantial complexity of having multiple streams to process and the incremental capital cost of the additional process equipment required for such an operating approach.

European Patent No. EP 1319648 B1 presents a process for producing acrylic acid wherein the effluent of a two-stage propylene oxidation process is first fed to a quench tower, wherein acrylic acid is captured via direct contact with process water. The resulting aqueous acrylic acid stream is then subjected to azeotropic distillation to remove wastewater from the aqueous acrylic acid, and the wastewater is recycled to the top of the quenching tower. A second aqueous acrylic acid stream is also withdrawn from the upper section of the quench tower and distilled; the removed water from this stream is also recycled to the top of the quench tower. Thus, this process involves withdrawing multiple product streams, both of which comprise water and acrylic acid, and both of which require further processing to produce acrylic acid of the commercially useful purity.

Industry would welcome processes which produce aqueous acrylic acid with less impurities and by-products so as to minimize problems in downstream purification steps involving accumulation of foulants, such as precipitates and polymer solids, which interfere with equipment performance and reduce the amount of inhibitor available for preventing polymerization of the (meth)acrylic acid product during later stages of processing, including purification, transport and storage. It is also desirable for such processes to be as simple as possible, i.e., to require as few process steps and as little equipment as possible, to thereby minimize capital and operating expenses.

SUMMARY OF THE INVENTION

The present invention provides a method for producing aqueous acrylic acid from a gaseous material stream comprising: a) providing a gaseous stream to a condenser, wherein the gaseous material stream comprises at least acrylic acid, water, acrolein, formaldehyde; and b) operating the condenser and producing a gaseous vent stream comprising uncondensed components, and a condensed aqueous acrylic acid stream comprising acrylic acid, wherein the aqueous acrylic acid stream comprises not more than 0.1% by weight formaldehyde, based on the total weight of the aqueous acrylic acid stream. The condensed aqueous acrylic acid stream may, for example, comprise between 75% and 95% by weight acrylic acid, based on the total weight of the condensed aqueous acrylic acid stream. The gaseous material stream may be the product of a hydrocarbon oxidation reaction, such as the catalytic vapor phase oxidation of a $C_2$-$C_4$ alkane or alkene to produce (meth)acrylic acid.

The method of the present invention may further comprise: c) stripping the aqueous acrylic acid stream in an acrolein removal column to obtain a reduced-acrolein content aqueous acrylic acid stream and a condensate stream comprising acrolein, and d) recycling said condensate stream comprising acrolein to the acrylic acid condenser.

BRIEF DESCRIPTION OF THE DRAWINGS

A more complete understanding of the present invention will be gained from the embodiments discussed hereinafter and with reference to the accompanying FIGURE which is a schematic representation of the condenser suitable for use with the method of the present invention.

DETAILED DESCRIPTION OF THE INVENTION

The following definitions and meanings are provided for clarity and will be used hereinafter.

As used herein, the term "$C_2$ to $C_4$ alkane" means a straight chain or branched chain alkane having from 2 to 4 carbons atoms per alkane molecule, for example, ethane, propane and butane, which are typically in the vapor phase at ordinary temperatures and pressures (e.g., at least 10° C. and 1 atmosphere). Similarly, the term "$C_2$ to $C_4$ alkene" means a straight chain or branched chain alkene having from 2 to 4 carbons atoms per alkene molecule, for example, ethene, propene and butene.

Endpoints of ranges are considered to be definite and are recognized to incorporate within their tolerance other values within the knowledge of persons of ordinary skill in the art, including, but not limited to, those which are insignificantly different from the respective endpoint as related to this invention (in other words, endpoints are to be construed to incorporate values "about" or "close" or "near" to each respective endpoint). The range and ratio limits, recited herein, are combinable. For example, if ranges of 1-20 and 5-15 are recited for a particular parameter, it is understood that ranges of 1-5, 1-15, 5-20, or 15-20 are also contemplated and encompassed thereby.

The method of the present invention produces an aqueous (meth)acrylic product having reduced quantities of impurities and by-products, particularly, less formaldehyde, than conventional processes by subjecting gaseous material streams comprising (meth)acrylic acid to a combination of one or more condensation steps using direct or indirect cooling with external heat exchangers and/or contact between the gaseous stream with the condensate in a column. The cooling obviates the need to add water, as is done in direct water-based absorption methods, which in turn minimizes the amount of formaldehyde that transfers from the gas phase into the aqueous (meth)acrylic acid. Further purifying steps, such as azeotropic distillation, non-azeotropic distillation, or crystallization, may be performed after the condensation, to remove additional water, by-products and impurities, as desired. Thus, the present invention provides a method for reducing solids formation (polymer and fouling material) during downstream processing of aqueous (meth)acrylic acid, for example during purification processes (e.g., in distillation columns, on trays/packing, within reboilers & piping), transport and storage of aqueous (meth)acrylic acid.

With reference now to the FIGURE, a schematic representation of one embodiment of the condensation step of the method of the present invention is provided. More particularly, a material stream 10 comprising (meth)acrylic acid and one or more by-products and impurities including, but not limited to, formaldehyde is provided to a condenser column 12. Additional by-products and impurities may be present in the material stream 10 including, but not limited to, unreacted reactants and intermediate products, steam, carbon dioxide, acrolein, acetic acid, propionic acid, other aldehydes and organics, maleic acid and maleic anhydride. The material stream 10 typically further contains one or more noncondensable components, such as nitrogen, oxygen and other substances having a boiling point, at atmospheric pressure (i.e., 1 bar), of at least −40° C., for example, at least −30° C., or even at least −20° C., in amounts from 20% to 95% by weight, such as from 50% to 95%, or even 70% to 90% by weight, based on the total weight of the material stream 10. The material stream 10 should be hot, i.e., having a temperature of from 50° C. to 450° C., such as, for example, 100° C. to 350° C., or even 150° C. to 350° C.

The source of the material stream 10 comprising (meth)acrylic acid, formaldehyde and acrolein is not critical. The material stream 10 may be, for example, without limitation, the exit gas from a hydrocarbon oxidation reactor wherein the hydrocarbon was a $C_2$ to $C_4$ alkane or alkene (i.e., ethane, propane, or butane, or ethylene, propylene, n-butylene or iso-butylene, respectively). Such a material stream might, for example, without limitation, have the following typical composition, based on the total weight of the material stream: from 1% to 30% by weight of (meth)acrylic acid, from 0.05% to 1% by weight of unreacted propylene or isobutylene, from 0.05% to 1% by weight of unreacted (meth)acrolein, from 0.05% to 10% by weight of oxygen, from 0.05% to 2% by weight of acetic acid, from 0.01% to 2% by weight of propionic acid, from 0.05% to 1% by weight of formaldehyde, from 0.05 to 2% by weight of aldehydes, from 0.01 to 0.5% by weight of maleic anhydride and from 20% to 98%, such as 50% to 90% by weight of inert diluent gases (such as nitrogen or carbon oxides).

The condenser 12 is an apparatus that allows for one or more cooling steps for a gas stream by either direct cooling (such as heat exchanger) or indirect cooling (such as liquid pump around loop), and also allows for contacting of the condensate and gas streams in a conventional column with internals such as trays, packing, etc. Moreover, the condenser 12 may be of various configurations, well-known to persons of ordinary skill in the relevant art, such as where cooling occurs only at the top of the condenser 12, or only at the bottom, or even throughout the condenser column 12 with multiple external loops.

The condenser column 12 may be made of any suitable material including, but not limited to, 316 Stainless Steel (UNS31600), 316L Stainless Steel (UNS S31603), 317 Stainless Steel (UNS31700), 317L+ Stainless Steel (UNS S31725 & S31726), Al6XN (UNS N08367), Inconel 625 (UNS N06625), 904L (UNS N08904), Duplex 2205 (UNS S31803), Duplex 2507 (UNS S32750), Duplex 2304 (UNS S32304 ), Duplex alloy 329 (UNS S32900), Alloy 20 CB-3 (UNS N08020), and Hastelloy B2 (UNS N10665). Typically, the condenser column includes internal components such as distributors, baffles, solid packing materials, trays, etc., as necessary and determinable by persons of ordinary skill in the relevant art. In addition, the condenser column 12 is equipped with one or more external heat exchangers 14, 16 for indirect cooling and consequent recovery of the (meth)acrylic acid from the material stream 10.

For example, the gaseous material stream 10 may be cooled by contacting condensed liquid passing through tubular cooling exchanger 14 positioned at the bottom of condenser column 12, whereupon uncondensed gaseous materials ("light ends") continue to rise through condenser column 12 and condensed liquid materials accumulate in the bottom portion, or "sump" 22 of condenser column 12. A portion of the accumulated liquid materials are pumped and drawn out of the sump 22 to form aqueous (meth)acrylic acid 18. Uncondensed gaseous materials 24 exit from the top portion 26 of the condenser column 12 and enter a second heat exchanger 16 in which they are cooled and then fed to a separator (not shown per se) from which exits a residual off gas 20 and a condensed stream 28, which is recycled back to the condenser column 12. The residual off gas 20 may be provided to another process, such as, for example, being recycled to an oxidation reactor, or may be transferred to a disposal process, such as for example a thermal oxidizer.

The aqueous (meth)acrylic acid product 18 produced by this condensation step is more concentrated, i.e., having 75% to 95% by weight of (meth)acrylic acid, and has reduced levels of formaldehyde than the aqueous (meth)acrylic acid produced by conventional processes involving absorption which contain about 65% to 80% by weight of (meth)acrylic acid, based on the total weight of the aqueous (meth)acrylic acid. The aqueous (meth)acrylic acid stream contains not more than 0.1% by weight formaldehyde, such as, for example not more than 0.05%, or even not more than 0.01% by weight, based on the total weight of the aqueous (meth) acrylic acid. These lower formaldehyde levels in the aqueous (meth)acrylic acid product 18 lessen the formation of polymer and other fouling solids (e.g., the reaction products of formaldehyde and phenolic inhibitors) in downstream process equipment, such as azeotropic distillation columns, strippers, and crystallizers, which further yields higher asset utilization and lower operating cost. The higher (meth)acrylic acid concentration and lower impurities (e.g., formaldehyde) level also reduce the overall energy usage in the downstream purification/separation steps.

The crude aqueous (meth)acrylic acid 18 may be subjected to further purification using conventional means such as, without limitation, melt crystallization, distillation, stripping, azeotropic distillation, extraction, or combinations of thereof (e.g., distillation followed by crystallization) to remove additional by-products and impurities such as acetic acid, acrolein and unreacted alkane or alkene.

The process and method of the present invention will be clarified by the following examples, which are a combination of actual commercial-process data and computer models capable of predicting process results based on known equipment specifications and known operational data. The computer model used by applicants is commercially known as Aspen plus 2004.1 Simulation Engine and is available from Aspen Technology, located in Burlington, Mass., U.S.A.

EXAMPLES

Comparative Example 1

Conventional Absorber

Apparatus Specifications and General Operation

The equipment consists of an absorber which is a 316L stainless steel column with a 10-foot 6-inch (3.2 meters) diameter top section that is 102-foot 3-inch (31.166 meters) long, a 4-foot 4-inch (1.321 meters) long conical transition section, and a 15-foot 6-inch (4.724 meters) diameter by 30-foot 4-inch (9.246 meters) long bottom section. The bottom section of the column has an external liquid pump around loop to provide cooling for the reactor exit gas, and consists of a 1100 gallon per minute ("gpm") (250 m³/h SI units) pump drawing liquid from the bottom of the column, a 2807 square foot (261 square meter), 316L stainless steel tubular heat exchanger providing up to 30 MM BTU/h (8.78 MW) cooling using 31° C. (88° F.) cooling tower water, and return of the pump around liquid stream back to the bottom section above the packed bed described below.

Reactor exit gas is introduced to the column at the lower portion of the bottom section, and then passes through a V-grid vapor distributor followed by a 10-foot (3.048 meter) deep bed of 316 stainless steel #4 cascade mini rings, all contained in the large diameter bottom section. The gas then moves up the column via the transition section and passes in series through two 23-foot (7.010 meter) deep beds of 316 stainless steel #3 cascade mini rings (commercially available from Koch-Glitsch, LP, located in Wichita, Kans.), followed by two 14-foot 4-inch (4.369 meters) deep beds of 316 stainless steel Sulzer BX structured packing (commercially available from Sulzer Chemtech Ltd, located in Winterthur, Switzerland). The gas leaving the top bed, typically referred to as 'off gas', exits the top of the column and a portion is recycled to the feed of the reactor, while the remainder is sent to a thermal oxidizer.

Water feed to the column is introduced at the top and distributed to the top bed with a 316 stainless steel Nutter MTS-109 liquid distributor (equivalent commercially available from Jaeger Products, located in Houston, Tex.). After the liquid passes through each bed in the top section, the liquid is collected with a 316 stainless steel Nutter CFT-1206 chimney tray (equivalent commercially available from Jaeger Products, located in Houston, Tex.), and redistributed to the next bed with a 316 stainless steel MTS-109 liquid distributor (equivalent commercially available from Jaeger Products, located in Houston, Tex.). Liquid leaving the top section is added to liquid from the pump around circulation loop and distributed to the bottom bed with a 316 stainless steel Nutter HLT-538 liquid distributor (equivalent commercially available from Jaeger Products, located in Houston, Tex.). As liquid accumulates in the bottom, sump, of the column it is drawn via pump from the system by level control. The liquid leaving the bottom of the absorber is referred to as aqueous acrylic acid. The aqueous acrylic acid may be sent to downstream processes for further purification or, optionally, may be sent to an integrated acrolein removal column for efficient removal of acrolein.

In the embodiment of this example, the optional integrated acrolein removal column is utilized. The integrated acrolein removal column is a 4-foot 9-inch (1.448 meters) diameter, 304L stainless steel column with a 21-foot 8-inch (6.604 meters) packed bed of 304 stainless steel #2 Cascade Mini Rings and is equipped with a 411 square foot (38.2 square meter), 304L stainless steel thermosyphon reboiler, a 949 square foot (88.2 square meter), 304L stainless steel main condenser and a 293 square foot, (27.2 square meter), 304L stainless steel vent condenser. The absorber bottoms material is feed at the top of the column, which is operated at about 200 mmHg (26,664 Pa) absolute pressure, passes through the packing and is then heated at the bottom of the column by the reboiler to vaporize about 5-10%, by volume, of the stream. The vapor exiting the reboiler passes through the packed bed to provide stripping and is then condensed by the main and vent condensers. The condensate, which comprises acrolein, is returned to the bottom section of the absorber by addition to the return line for the pump around stream; by introducing the condensate in this manner, the acrolein is allowed to re-vaporize within the absorber. The liquid exiting the bottom of the acrolein removal column is referred to as reduced acrolein content aqueous acrylic acid and is sent to downstream processes for further purification.

Actual Operation and Performance

Based on the above-described equipment and actual operational data, the model assumed that reactor exit gas at 290° C. (554° F.) was introduced to the bottom of the absorber column with a mass flow of 253,641 lb/h (115,050 kg/h SI units), at a pressure of 4.2 psig (130,283 Pa SI units) and estimated to have the following composition:

| Reactor Exit Gas Composition 1 | |
|---|---|
| Component | vol % |
| Nitrogen | 70.9% |
| Water | 16.8% |
| Acrylic Acid | 6.87% |
| Oxygen | 1.80% |
| Carbon Dioxide | 1.45% |
| Carbon Monoxide | 0.723% |
| Propane | 0.548% |
| Propylene | 0.245% |
| Acrolein | 0.104% |
| Acetic Acid | 0.274% |
| Formaldehyde | 0.224% |
| Maleic Acid | 0.0452% |
| Acetaldehyde | 0.0154% |
| Acetone | 0.0031% |

The cooling in the bottom section of the absorber column was controlled to keep the column top temperature at 62° C. (144° F.), with a resulting bottom temperature of 73° C. (163° F.). The gas flow exiting the top of the absorber was calculated to be 212,047 lb/h (96,183 kg/h) at 1.9 psig (114,425 Pa) and had the following estimated composition:

| Off Gas Composition 1 | |
|---|---|
| Component | vol % |
| Nitrogen | 75.5% |
| Water | 19.0% |
| Acrylic Acid | 0.175% |
| Oxygen | 1.92% |
| Carbon Dioxide | 1.54% |
| Carbon Monoxide | 0.771% |
| Propane | 0.584% |
| Propylene | 0.261% |
| Acrolein | 0.110% |
| Acetic Acid | 0.0007% |
| Formaldehyde | 0.0341% |
| Maleic Acid | 0% |
| Acetaldehyde | 0.0152% |
| Acetone | 0.0032% |

The absorber column was provided with a 19,400 lb/h (8,800 kg/h) feed of water, which included hydroquinone (HQ) inhibitor and the aqueous acrylic acid product stream exiting the absorber column had a 65,069 lb/h (29,515 kg/h) flow and the following composition:

| Aqueous Acrylic Acid Composition 1 | | | |
|---|---|---|---|
| Component | wt % | lb/h | kg/hr |
| Acrylic Acid | 66.0% | 42,917 | 19,508 |
| Water | 30.2% | 19,657 | 8,935 |

-continued

Aqueous Acrylic Acid Composition 1

| Component | wt % | lb/h | kg/hr |
|---|---|---|---|
| Formaldehyde | 0.812% | 528 | 240 |
| Acrolein | 0.0477% | 31 | 14 |
| Maleic Acid | 0.700% | 455 | 207 |
| Acetic Acid | 2.26% | 1,470 | 668 |
| Acetaldehyde | 0.0119% | 8 | 4 |

The aqueous acrylic acid product was then fed to the acrolein removal column to remove acrolein. The reduced-acrolein content aqueous acrylic acid stream removed from the acrolein removal column bottom had a 60,886 lb/h (27,617 kg/h) flow and the following composition:

Reduced-Acrolein content
Aqueous Acrylic Acid Composition 1

| Component | wt % | lb/h | kg/hr |
|---|---|---|---|
| Acrylic Acid | 67.1% | 40,855 | 18,570 |
| Water | 29.2% | 17,779 | 8,081 |
| Formaldehyde | 0.804% | 490 | 223 |
| Acrolein | 0.0095% | 6 | 3 |
| Maleic Acid | 0.730% | 444 | 202 |
| Acetic Acid | 2.10% | 1,279 | 581 |
| Acetaldehyde | 0.0069% | 4 | 2 |

Examples 1 and 2

Condenser

Apparatus Specifications and General Operation

The equipment consists of a condenser which is a 316L stainless steel column with a 10-foot 6-inch (3.200 meters) diameter top section that is 102-feet 3-inches (31.166 meters) long, a 4-foot 4-inch (1.321 meters) long conical transition section, and a 15-foot 6-inch (4.724 meters) diameter by 30-foot 4-inch (9.246 meters) long bottom section. The top of the condenser column is equipped with a 11,832 square foot (1099 square meters) tubular exchanger, top cooler, providing up to 33 MM BTU/h (9.66 MW) cooling using 31° C. (88° F.) cooling water to cool the gas leaving the top of the column, and a separation vessel is designed to separate the vapor and liquid and collect the condensate for return to the top of the column by pump. The bottom section of the column has an external liquid pump around loop to provide cooling for the reactor exit gas, and consists of a 1100 gpm (250 m$^3$/h) pump drawing liquid from the bottom of the column, a 2807 square foot (261 square meters), 316L stainless steel tubular heat exchanger providing up to 30 MM BTU/h (8.78 MW) cooling using 31° C. (88° F.) cooling tower water, and return of the pump around liquid stream back to the bottom section above the packed bed described below.

Reactor exit gas is introduced to the condenser column at the lower portion of the bottom section, and then passes through a V-grid vapor distributor followed by a 10-foot (3.048 meter) deep bed of 316 stainless steel #4 cascade mini rings, all contained in the large diameter bottom section. The gas then moves up the column via the transition section and passes in series through two 23-foot (7.010 meters) deep beds of 316 stainless steel #3 cascade mini rings, followed by two 14-foot 4-inch (4.369 meters) deep beds of 316 stainless steel Sulzer BX structured packing. The gas leaves the top bed, exits the top of the column, and is then piped to the top cooler. After being cooled, the gas stream then passes through the separator to remove liquid condensate before leaving the system as 'off gas', and a portion is recycled to the feed of the reactor while the remainder is sent to a thermal oxidizer. The condensate collected by the separator vessel is feed to the top of the column and distributed to the top bed using a 316 stainless steel Nutter MTS-109 liquid distributor. After the liquid passes through each bed in the top section, the liquid is collected with a 316 stainless steel Nutter CFT-1206 chimney tray and redistributed to the next bed with a 316 stainless steel MTS-109 liquid distributor. Liquid leaving the top section is added to liquid from the pump around circulation loop and distributed to the bottom bed with a 316 stainless steel Nutter HLT-538 liquid distributor. As liquid accumulates in the bottom, sump, of the column it is drawn via pump from the system by level control. The liquid leaving the bottom of the condenser column is referred to as aqueous acrylic acid. The aqueous acrylic acid may be sent to downstream processes for further purification or, optionally, may be sent to an integrated acrolein removal column for efficient removal of acrolein. In the embodiment of this example, the optional integrated acrolein removal column is utilized. The integrated acrolein removal column is a 4-foot 9-inch (1.448 meters) diameter, 304L stainless steel column with a 21-foot 8-inch (6.604 meters) packed bed of 304 stainless steel #2 cascade mini rings and is equipped with a 411 square foot (38.2 square meter) 304L stainless steel thermosyphon reboiler, a 949 square foot (88.2 square meter) 304L stainless steel main condenser and a 293 square foot (27.2 square meters), 304L stainless steel vent condenser. The condenser column bottoms material is feed at the top of the acrolein removal column, which is operated at about 200 mmHg (26,664 Pa) absolute pressure, passes through the packing and is then heated at the bottom of the column by the reboiler to vaporize about 5-10% by weight of the stream. The vapor exiting the reboiler passes through the packed bed to provide stripping and is then condensed by the main and vent condensers. The condensate, which comprises acrolein, is returned to the bottom section of the condenser column by addition to the return line for the pump around stream. By introducing the condensate in this manner, the acrolein is allowed to re-vaporize within the condenser column. The liquid exiting the bottom of the acrolein removal column is referred to as reduced acrolein content aqueous acrylic acid and is sent to downstream processes for further purification.

Example 1

Actual Modeled Operation and Performance
("Medium Aqueous Strength")

Based on the above-described condenser equipment, operation of the inventive condenser system was simulated with the same reactor exit gas composition and mass flowrate (253,641 lb/h (115,050 kg/h) as that used in Comparative Example 1; In this example, the reactor exit gas is introduced to the bottom of the condenser column at a temperature of 290° C. (554° F.) and a pressure of 7.3 psig (151,657 Pa). The model was run with sufficient cooling at the bottom section of the condenser column to control the column top temperature at 68° C. (154° F.), and 25.7 MM BTU/h (7.53 MW) of cooling through the top cooler, resulting in a bottom temperature of 80.7° C. (177° F.). The off gas exiting the top of the vapor-liquid separator after the top cooler is calculated to be flowing at 200,421 lb/h (90,910 kg/h), at a pressure of 1.5 psig (111,667), and the model predicts the following composition:

| Off Gas Composition 2 | |
|---|---|
| Component | vol % |
| Nitrogen | 82.4% |
| Water | 11.5% |
| Acrylic Acid | 0.199% |
| Oxygen | 2.09% |
| Carbon Dioxide | 1.68% |
| Carbon Monoxide | 0.840% |
| Propane | 0.636% |
| Propylene | 0.285% |
| Acrolein | 0.119% |
| Acetic Acid | 0.0067% |
| Formaldehyde | 0.262% |
| Maleic Acid | 0% |
| Acetaldehyde | 0.0179% |
| Acetone | 0.0035% |

For the purpose of polymer inhibition, the column is provided with a 400 lb/h (181 kg/h) feed of de-ionized water with 5% by weight of hydroquinone (HQ) inhibitor. Aqueous acrylic acid exits the bottom of the condenser column at a flowrate of 58,176 lb/h (26,388 kg/h) and with the following composition:

| Aqueous Acrylic Acid Composition 2 | | | |
|---|---|---|---|
| Component | wt % | lb/h | kg/hr |
| Acrylic Acid | 74.5% | 43,317 | 19,690 |
| Water | 21.8% | 12,697 | 5,772 |
| Formaldehyde | 0.0228% | 13 | 6 |
| Acrolein | 0.0414% | 24 | 11 |
| Maleic Acid | 0.785% | 457 | 208 |
| Acetic Acid | 2.53% | 1,471 | 669 |
| Acetaldehyde | 0.0022% | 1 | 1 |

Per the simulation, the aqueous Acrylic acid stream of this example is then fed to the acrolein removal column, wherein acrolein is stripped and recycled to the condenser column. Reduced-acrolein content aqueous acrylic acid will be removed from the bottom of the acrolein removal column at a flowrate of 53,620 lb/h (24,322 kg/h) and will have the following composition:

| Reduced-Acrolein content Aqueous Acrylic Acid Composition 2 | | | |
|---|---|---|---|
| Component | w % | lb/h | kg/hr |
| Acrylic Acid | 76.2% | 40,858 | 18,572 |
| Water | 20.4% | 10,938 | 4,972 |
| Formaldehyde | 0.0003% | 0.2 | 0.1 |
| Acrolein | 0.0121% | 6 | 3 |
| Maleic Acid | 0.829% | 445 | 202 |
| Acetic Acid | 2.55% | 1,367 | 622 |
| Acetaldehyde | 0% | — | — |

Under the conditions of this example, it is clear that the method of the present invention provides significantly lower formaldehyde levels in aqueous acrylic acid than the prior-art absorption process, and that this benefit is maintained even when aqueous acrylic acid is stripped in an acrolein removal column.

Example 2

Actual Operation and Performance ("High Aqueous Strength")

Based on the above-described condenser equipment, operation of the inventive condenser system was again simulated with the same reactor exit gas composition and mass flow rate (253,641 lb/h (115,050 kg/h)) as that used in Comparative Example 1;. In this example, the reactor exit gas is introduced to the bottom of the condenser column at a temperature of 290° C. (554° F.) and a pressure of 7.3 psig (151,657 Pa).

The model was run with no cooling in the bottom section of the condenser column and the top cooler is simulated to provide 43.5 MM BTU/h (12.7 MW) resulting in a 60° C. (140° F.) top cooler exit temperature and 103° C. (217° F.) column bottom temperature. The off gas exiting the top of the vapor-liquid separator after the top cooler is calculated to be flowing at 211,611 lb/h, (95,985 kg/h) at a pressure of 1.5 psig (111,667 Pa) and the model predicts the following composition:

| Off Gas Composition 3 | |
|---|---|
| Component | vol % |
| Nitrogen | 76.3% |
| Water | 17.9% |
| Acrylic Acid | 0.285% |
| Oxygen | 1.93% |
| Carbon Dioxide | 1.56% |
| Carbon Monoxide | 0.778% |
| Propane | 0.589% |
| Propylene | 0.264% |
| Acrolein | 0.110% |
| Acetic Acid | 0.0842% |
| Formaldehyde | 0.243% |
| Maleic Acid | 0% |
| Acetaldehyde | 0.0165% |
| Acetone | 0.0033% |

For the purpose of polymer inhibition, the column will only be provided with a 400 lb/h (181 kg/h) feed of de-ionized water with 5% by weight hydroquinone (HQ) inhibitor. Aqueous acrylic acid exits the bottom of the condenser column at a flowrate of 46,856 lb/h (21,254 kg/h) and with the following composition:

| Aqueous Acrylic Acid Composition 3 | | | |
|---|---|---|---|
| Component | wt % | lb/h | kg/hr |
| Acrylic Acid | 94.2% | 44,152 | 20,069 |
| Water | 2.19% | 1,026 | 466 |
| Formaldehyde | 0.0058% | 3 | 1 |
| Acrolein | 0.0304% | 14 | 6 |
| Maleic Acid | 0.982% | 460 | 209 |
| Acetic Acid | 2.45% | 1,147 | 521 |
| Acetaldehyde | 0.0014% | 1 | 0 |

Per the simulation, the aqueous Acrylic acid stream of this example is then fed to the acrolein removal column, wherein acrolein is stripped and recycled to the condenser column. Reduced-acrolein content aqueous acrylic acid will be removed from the bottom of the acrolein removal column at a flowrate of 42,430 (19,246 kg/h) lb/h and will have the following composition:

| Reduced-Acrolein content Aqueous Acrylic Acid Composition 3 | | | |
|---|---|---|---|
| Component | wt % | lb/h | kg/hr |
| Acrylic Acid | 95.0% | 40,309 | 18,322 |
| Water | 1.59% | 675 | 307 |
| Formaldehyde | 0.0012% | 0.5 | 0.2 |
| Acrolein | 0.0196% | 8 | 4 |
| Maleic Acid | 1.05% | 446 | 203 |
| Acetic Acid | 2.35% | 997 | 453 |
| Acetaldehyde | 0.0006% | 0 | 0 |

Under the conditions of this example, it is clear that the method of the present invention provides significantly lower formaldehyde levels in aqueous acrylic acid than the prior-art absorption process, and that this benefit is maintained even when aqueous acrylic acid is stripped in an acrolein removal column.

We claim:

1. A method for producing aqueous acrylic acid from a gaseous material stream comprising:
   a) providing a gaseous stream to a condenser, wherein the gaseous material stream comprises at least acrylic acid, water, formaldehyde; and
   b) operating the condenser and producing a gaseous vent stream comprising uncondensed components, and a condensed aqueous acrylic acid stream comprising acrylic acid,
wherein the aqueous acrylic acid stream comprises not more than 0.1% by weight formaldehyde, based on the total weight of the aqueous acrylic acid stream, and wherein the balance of the formaldehyde originally in the gaseous material stream is contained in the gaseous vent stream.

2. The method of claim 1, wherein the aqueous acrylic acid stream comprises between 75% and 95% by weight acrylic acid, based on the total weight of the aqueous acrylic acid stream.

3. The method of claim 1 wherein said aqueous acrylic acid stream comprises not more than 0.05% by weight formaldehyde.

4. The method of claim 1 wherein said aqueous acrylic acid stream comprises not more than 0.01% by weight formaldehyde.

5. The method of claim 1 further comprising:
   c) stripping the aqueous acrylic acid stream in an acrolein removal column to obtain a reduced-acrolein content aqueous acrylic acid stream and a condensate stream comprising acrolein, and
   d) recycling said condensate stream comprising acrolein to the acrylic acid condenser.

6. The method of claim 1 further comprising oxidizing at least one hydrocarbon selected from propylene and propane in a catalytic vapor-phase shell-and-tube reaction system to produce said gaseous material stream comprising acrylic acid, water and formaldehyde.

7. The method of claim 1, wherein the gaseous stream further comprises non-condensable materials which have a boiling point, at atmospheric pressure, of no greater than −40° C.

8. The method of claim 1, wherein the gaseous material stream has a temperature of from 50° C. to 450° C.

* * * * *